United States Patent [19]

Szabo et al.

[11] 4,197,110
[45] Apr. 8, 1980

[54] N-ACYLATED HETEROCYCLES AND HERBICIDAL-ANTIDOTE USES THEREOF

[75] Inventors: Karoly Szabo, Vienna, Austria; Bertrand Castro, Messein; Daniel H. Balde, Paris, both of France

[73] Assignee: Produits Chimiques Ugine Kuhlmann, Paris, France

[21] Appl. No.: 683,599

[22] Filed: May 5, 1976

[30] Foreign Application Priority Data

May 7, 1975 [FR] France ............................ 75 14297

[51] Int. Cl.$^2$ .................... A01N 9/22; A01N 9/12; C07D 263/06; C07D 265/06
[52] U.S. Cl. .................... 71/88; 260/239 BC; 260/239 BD; 260/304 R; 260/333; 544/88; 544/90; 544/54; 544/50; 544/335; 544/283; 548/300; 548/333; 71/90; 71/91; 71/92; 548/178; 548/180; 548/200; 548/215; 548/217
[58] Field of Search ............ 71/88; 260/307 FA, 333, 260/244 R; 544/88

[56] References Cited

U.S. PATENT DOCUMENTS

| | | | |
|---|---|---|---|
| 3,707,541 | 12/1972 | Lajiness | 260/244 R |
| 3,825,555 | 7/1974 | Lajiness | 260/307 F |
| 3,859,252 | 1/1975 | Dorschner et al. | 260/293.66 |
| 3,884,671 | 5/1975 | Albright et al. | 71/88 |
| 3,959,304 | 5/1976 | Teach | 260/307 FA |
| 4,069,036 | 1/1978 | Dorschner et al. | 260/307 FA |
| 4,124,372 | 11/1978 | Pallos et al. | 71/88 |

OTHER PUBLICATIONS

Lambert et al. C.A. 75, 98479j (1971).

*Primary Examiner*—Mark L. Berch
*Attorney, Agent, or Firm*—Beveridge, DeGrandi, Kline & Lunsford

[57] ABSTRACT

Heterocyclic compounds of the general formula:

wherein:
$R_1$ represents alkyl, haloalkyl, alkenyl, haloalkenyl, arylalkyl, arylhaloalkyl, cycloalkyl, halocycloalkyl, aryl, haloaryl, alkoxyalkyl or haloalkoxyalkyl;
$X_1$ is chlorine, bromine, or fluorine;
$X_2$ and $X_3$ are hydrogen, chlorine, bromine or fluorine;
A represents oxygen or sulphur, S-O or N-$R_8$;
$R_8$ is hydrogen, alkyl, haloalkyl, hydroxyalkyl, alkoxyalkyl, arylalkyl, aryl or $$-\underset{\underset{O}{\|}}{C}-R_1;$$

B represents m is 0, 1 or 2;
n and p are 0 or 1;
$R_2$, $R_3$, $R_4$, $R_5$, $R_6$, $R_7$, $R'_2$, $R'_3$, $R'_4$, $R'_5$ are the same or different and are hydrogen, alkyl, alkoxyalkyl, haloalkyl, or hydroxyalkyl;
and Y and Z are the same or different and are hydrogen, halogen, alkyl or alkoxy.

These compounds are used as antidotes against herbicides.

12 Claims, No Drawings

N-ACYLATED HETEROCYCLES AND HERBICIDAL-ANTIDOTE USES THEREOF

The present invention relates to new heterocyclic compounds, their process of preparation, compositions containing same, and their use as antidotes against herbicides.

Numerous herbicidal products exist today for the control or elimination of unwanted plant growth. Generally these products may be classified into two categories: total herbicides which destroy all the plants and selective herbicides which destroy only the undesirable adventitious plants in cultivated ground. Selective herbicides are of greater interest for commercial purposes. Unfortunately, it very often happens that this selectivity may not be perfect at the dose used and the selective herbicides may exhibit a certain phytotoxicity with respect to the cultivated plant. In addition, the selective herbicides are often only effective against certain adventitious plants, which limits their use.

There have now been found, according to the present invention, heterocyclic compounds which have the remarkable property of increasing the selectivity of numerous families of herbicides inasmuch as they protect the cultivated plant without harming the effectiveness of the herbicide on undesirable plants.

On account of this property such compounds are called antidotes against herbicides. Use of their antidotes permits, on the one hand, the improvement of the yields in the desired cultivated plants, and on the other hand, the extension of the field of use of herbicides which are noteworthy but have been considered up to now as too phytotoxic to be able to be used on certain cultivated plants.

The compounds according to the invention may be represented by the general formula:

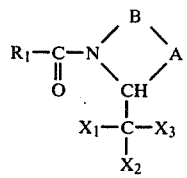  (I)

wherein:

$R_1$ represents alkyl, haloalkyl, alkenyl, haloalkenyl, arylalkyl, arylhaloalkyl, cycloalkyl, halocycloalkyl, aryl, haloaryl, alkoxyalkyl, or haloalkoxyalkyl;

$X_1$ represents chlorine, bromine or fluorine;

$X_2$ represents hydrogen, chlorine, bromine or fluorine;

$X_3$ represents hydrogen, chlorine, bromine or fluorine;

A represents oxygen, sulphur, S—O,

or N—$R_8$;

$R_8$ may be hydrogen, alkyl, haloalkyl, hydroxyalkyl, alkoxyalkyl, arylalkyl, aryl or

B represents

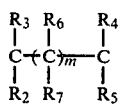

in which m is 0, 1 or 2, and $R_2$, $R_3$, $R_4$, $R_5$, $R_6$, $R_7$ are the same or different, and represent hydrogen, alkyl, alkoxyalkyl, haloalkyl, or hydroxyalkyl, two of these substituents attached to two adjacent carbon atoms being able in addition to form together with the carbon atoms to which they are linked, an aliphatic ring or else B represents:

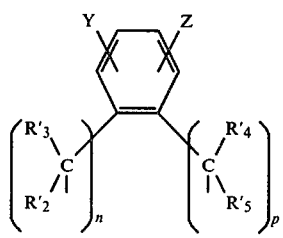

wherein n is 0 or 1, p is 0 or 1, $R'_5$, $R'_2$, $R'_3$, $R'_4$ are the same or different and represent hydrogen, alkyl, alkoxyalkyl, haloalkyl or hydroxyalkyl;

Y and Z are the same or different and represent hydrogen, halogen, akyl or alkoxy.

In the definitions of the substituents $R_1$, $R_2$, $R_3$, $R_4$, $R_5$, $R_6$, $R_7$, $R_8$, $R'_2$, $R'_3$, $R'_4$, $R'_5$, Y and Z the alkyl, alkenyl and alkoxy chains preferably contain 1 to 5 carbon atoms, the cycloalkyl groups may have 3 to 6 carbon atoms in the ring, the halogenated groups preferably contain 1 to 7 halogen atoms which may be chlorine, bromine or fluorine atoms, and aryl preferably signifies phenyl or phenyl substituted by one or two substituents which may be halogen atoms or alkyl or alkoxy groups having 1 to 5 carbon atoms.

In the formula (I) above $R_1$ may not be methyl when simultaneously $X_1$, $X_2$ and $X_3$ are chlorine atoms, A is an oxygen atom and B is the —$CH_2$—$CH_2$— group.

Included among the compounds of formula I are those in which A is oxygen and which are the oxazolidine type compounds.

Further included in formula I are compounds of the oxazolidine type wherein the halogen is chlorine.

Still further included in formula I are compounds of the oxazolidine type wherein $R_1$ is alkyl and haloalkyl, especially chloroalkyl.

The compounds of formula (I) may be prepared by the action of an α-halo-aldehyde of formula (II) on an amino compound of formula (III), according to the reaction (1)

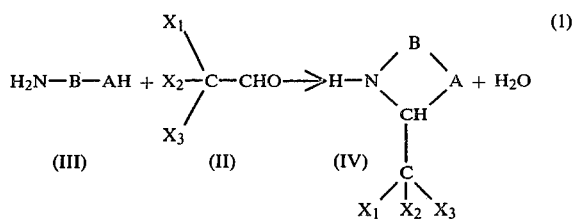

and the action of an acid chloride of formula $R_1—CO—Cl$ or an acid anhydride of formula $(R_1—CO)_2O$ on the intermediate product of formula (IV) obtained, according to the reactions (2) and (3) as follows:

(2) $(IV) + R_1—CO—Cl \rightarrow (I) + HCl$ (3) $(IV) + (R_1—CO)_2O \rightarrow (I) + R_1COOH$ In the formulae (II), (III), (IV) above, $X_1$, $X_2$ and $X_3$ and B have the same significance as in formula (I), and A represents an oxygen or sulphur atom, or a

group in which $R_8$ has the same significance as in formula (I).

The compounds of formula (I) for which A is a

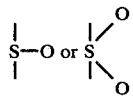

group may be obtained by oxidation of the compounds of formula (I) for which A is a sulphur atom.

The reaction (I) may be effected advantageously in the presence of an acid such as, for example, acetic acid, and in the presence of a solvent which codistills with water as, for example, benzene. The reaction is effected at the reflux temperature of the reaction mixture. The water produced is separated by distillation in proportion to its formation. The intermediate product of formula (IV) thus formed may be isolated by eliminating the solvent and the acid by distillation or else, which is often advantageous, by eliminating the acid by washing with water or by means of an aqueous solution of an alkali metal hydroxide, then the solvent by distillation. The intermediate product thus isolated in a crude state may be purified by distillation under reduced pressure or recrystallization from a suitable solvent, or engaged directly in the following reactions (2) and (3).

The reaction (2) is preferably effected in an inert solvent such as, for example, an ether, an aliphatic or aromatic hydrocarbon or a chlorinated derivative of an aliphatic or aromatic hydrocarbon, at a temperature between −30° C. and 60° C., preferably between −10° C. and 30° C. The hydrochloric acid formed in the reaction is neutralized, in proportion as it is formed, by a mineral base or a tertiary amine as, for example, triethylamine or pyridine. After separation, by extraction with water or by filtration, of the chloride of the mineral base or of the hydrochloride of the amine, the product of formula (I) formed is isolated, in the crude state, by elimination of the solvent by distillation. It may be purified, for example, by recrystallization, or used as it is.

The reaction (3) may be effected in the same solvents as the reaction (2). It is effected in the presence of not of a mineral acid as catalyst and at a temperature which may vary between 0° C. and 100° C. according to the reactivity of the intermediate product of formula (IV). After washing the reaction mixture with water, the product of formula (I) formed may be isolated and purified as previously indicated.

The compounds according to the invention may be used as antidotes against herbicides, for the treatment of crops. They may be used against numerous families of herbicides among which may be mentioned particularly the thiolcarbamates, the chloroacetanilides, the ureas, the triazines, the carbamates, the uracils, used separately or in admixture. The ratio antidote product/herbicide to be used may vary considerably according to the nature of the herbicide concerned. In a general way, this ratio is between 0.001 and 10, most often between 0.01 and 5.

The compounds according to the invention may be used in all the forms commonly used in agriculture. Thus they may be provided, conjointly with the herbicide or separately, in the form of wettable powder, a solution emulsifiable in water to form an emulsion, granules or any other form in use in the herbicidal field. In all these formulations there may be incorporated the additives commonly used with a view to facilitating the keeping, operation and penetration of the products in the plants, such as solid, particulate materials including inert minerals e.g. talc, silica, kieselguhr, diatomaceous earth, clay and the like. Various organic solvents or diluents such as mineral oils, and organic solvents may be employed to formulate compositions. Surface-active compounds, antioxidants and various stabilizers are illustrative of optional conventional materials that may be included in the compositions.

The compounds according to the invention may be applied at the same time as the herbicides or separately. They may be applied, for example, to the soil, before or after the emergence of the plant and before or after application of the herbicide. In particular, they may be applied to soils containing herbicidal residues so as to protect the cultivated plants against the remaining activity of these residues. They may also be used to treat the seeds of the cultivated plant (in liquid or dust form).

The cultivated plant or any part thereof may be treated.

The following Examples illustrate the invention without limiting it.

EXAMPLE 1

1st part: 120 g of glacial acetic acid (2 moles) is slowly added with stirring at the ambient temperature to a solution of 61 g of monoethanolamine (1 mole) in 500 ml of benzene, with slight cooling if necessary. Then 147.5 g of anhydrous chloral (1 mole) is added and the solution is refluxed the water which has formed being separated by azeotropic distillation by means of a Dean-Stark apparatus. The mixture is maintained under reflux for 4 hours.

The temperature is cooled to 20° C. and the reaction mixture is taken up in 500 ml of water. It is adjusted to pH 8 to 9 by addition of 5 N caustic potash (about 450 ml). It is decanted, the benzene layer is separated and washed with 500 ml of water. After filtration, the benzene is distilled under vacuum. 170 g of 2-trichloromethyl-1,3-oxazolidine is thus obtained (yield 89%). This product has a melting point of 73° C.

2nd part: 190.5 g of 2-trichloromethyl-1,3-oxazolidine (1 mole) prepared as indicated above, is dissolved in 2 liters of chloroform and 202 g of triethylamine (2 moles) is then added. While maintaining the temperature at about 0° C., 236 g of dichloro acetyl chloride (1.6 moles) dissolved in 400 ml of chloroform, is added with stirring in about one and a half hours. The mixture is stirred for 2 to 3 hours, while allowing the temperature to return to the ambient temperature, then it is taken up in 4 liters of water. After decantation the organic phase is separated and washed with 2 liters of water, then dried over magnesium sulphate. The chloroform is distilled under vacuum. During the distillation a crystalline product is formed which is separated. This product is recrystallized from a 50—50 chloroform-petrol ether mixture. 227 g (say a yield of 75%) of 2-trichloromethyl-3-dichloroacetyl-1,3-oxazolidine of melting point 117°–118° C. is thus obtained.

EXAMPLE 2

1st part: By operating as in the first part of Example 1 but replacing the 61 g of monoethanolamine by 75 g of monoisopropanolamine (1 mole), 182 g (say a yield of 90%) of 2-trichloromethyl-5-methyl-1,3-oxazolidine of melting point 54°–55° C. is obtained.

2nd part: 38 g of 2-trichloromethyl-5-methyl-1,3-oxazolidine (0.18 mole), prepared as indicated above, is dissolved in 400 ml of ether. 36 g of triethylamine (0.36 mole) added. While maintaining the temperature at about 0° C., 53 g of dichloroacetyl chloride (0.36 mole) dissolved in 100 ml of ether is added with stirring in about 1½ hours. The mixture is agitated for 2 to 3 hours, while allowing the temperature to return to the ambient temperature, then it is taken up in 1000 ml of water. After decantation, the organic phase is separated, washed with 500 ml of water and dried over magnesium sulphate. After removal of the ether by distillation 53 g of crude 2-trichloromethyl-3-dichloro-acetyl-5-methyl-1,3-oxazolidine is obtained (say a yield of 95%) in the form of a viscous oil with a refractive index $n_D^{22} = 1.527$. This product, purified by recrystallization from a 50—50 carbon tetrachloride-hexane mixture, gives a white solid melting at 78° C.

EXAMPLE 3

By operating as in the first part of Example 1, but replacing the 61 g of monoethanolamine by 89 g of 2-aminobutanol (1 mole), 184 g (say a yield of 84%) of 2-trichloromethyl-4-ethyl-1,3-oxazolidine is obtained, which has a boiling point of 77°–78° C. under 0.4 mm Hg and a refractive index of $n_D^{21} = 1.4958$.

By operating as in the second part of Example 2, but using 21.8 g of 2-trichloromethyl-4-ethyl-1,3-oxazolidine (0.1 mole) dissolved in 250 ml of ether, 12.2 g of triethylamine (0.12 mole) and 17.6 g of dichloroacetyl chloride (0.12 mole) dissolved in 50 ml of ether, after the removal of the ether, 30 g (say a yield of 91%) of crude 2-trichloromethyl-3-dichloromethyl-3-dichloroacetyl-4-ethyl-1,3-oxazolidine is obtained in the form of a very viscous red paste.

EXAMPLE 4

19.05 g of 2-trichloromethyl-1,3-oxazolidine (0.1 mole) prepared as indicated in Example 1, in solution in 100 ml of tetrahydrofuran (THF), is added, in about 15 minutes, to a solution of 27.9 g of 2,3,4,4,4-pentachlorobutanoyl chloride (0.1 mole) in 200 ml of THF. The reaction is effected with stirring in the presence of 10.1 g of triethylamine (0.1 mole), while maintaining the temperature of the reaction mixture in the neighborhood of 20° C. After the completion of the addition the mixture is stirred for 30 further minutes, then the precipitate of triethylamine hydrochloride is filtered off.

After evaporation of the solvent, 38.3 g (say a yield of 88% of crude 2-trichloromethyl-(2,3,4,4,4-pentachloro)-3-butanoyl-1,3-oxazolidine is obtained in the form of an orange-red viscous liquid. This product on recrystallization from ether gives a white product of a melting point of 140° C.

EXAMPLE 5

By operating as in the first part of Example 1, but replacing the 61 g of monoethanolamine by 75 g of 3-aminopropanol (1 mole), 177 g (yield 87%) of 2-trichloromethyl-1,3-tetrahydro-oxazine is obtained in the form of a liquid of boiling point 75°–76° C. under 0.8 mm of Hg and of refractive index $N_D^{21} = 1.5088$.

By operating as in the second part of Example 2, but using 20.5 g of 2-trichloromethyl-1,3-tetrahydro-oxazine (0.1 mole) dissolved in 30 ml of ether, 30.3 g of triethylamine (0.3 mole) and 29.5 g of dichloroacetyl chloride (0.2 mole) dissolved in 100 ml of ether, after the removal of the ether 32.5 g (yield 86%) of crude 2-trichloromethyl-3-dichloroacetyl-1,3-tetrahydro-oxazine is obtained in the form of an oil having a refractive index of $n_D^{22} = 1.532$.

EXAMPLE 6

By operating as in the first part of Example 1 but replacing the 61 g of monoethanolamine by 77 g of 2-amino-thioethanol (1 mole), 149 g (yield 72%) of 2-trichloromethyl-1,3-thiazolidine is obtained.

40 g of triethylamine (0.4 mole), then 43 g of dichloroacetyl chloride (0.3 mole) are added successively, while maintaining the temperature of the reaction mixture at about 0° C. to 41 g of 2-trichloromethyl-1,3-thiazolidine (0.2 mole), dissolved in 300 ml of ether. After the removal of the triethylamine hydrochloride formed in the reaction and washing the organic phase with water, the organic layer is concentrated by stripping part of the ether. By crystallization and filtration, 53 g (yield 82%) of 2-trichloromethyl-3-dichloroacetyl-1,3-thiazolidine of melting point 124° C. is obtained.

EXAMPLE 7

A solution containing 7 g of m-chloroperbenzoic acid (0.041 mole) in 100 ml of methylene chloride is added to a solution of 6.6 g of 2-trichloromethyl-3-dichloroacetyl-1,3-thiazolidine (0.02 mole), prepared as indicated in Example 6, in 100 ml of methylene chloride. The addition is made while stirring and maintaining the temperature of the reaction mixture between 0° and 5° C. After the end of the addition, the reaction mixture is maintained for 3 hours at the ambient temperature with stirring. The reaction mixture is filtered while cold and the precipitate is rinsed with some tens of ml of cold methylene chloride. The organic phase is then washed with a dilute aqueous solution of sodium carbonate, then with water, and dried over magnesium sulphate. After distillation in vacuo of the methylene chloride, 4.7 g (yield 65%) of 1,1-dioxo-2-trichloromethyl-3-dichloroacetyl-1,3-thiazolidine a pasty solid, is obtained.

EXAMPLE 8

By operating as in the first part of Example 1, but replacing the 61 g of monoethanolamine by 58 g of ethylenediamine (1 mole), 157 g (yield 84%) of 2-trichloromethyl-1,3-imidazolidine is obtained a solid melting at 106°–108° C.

20.2 g of triethylamine (0.2 mole) are added to 9.4 g of the preceding product (0.05 mole) dissolved in 250 ml of ether, and then, progressively, while stirring and cooling to 0° C., 22.1 g of dichloroacetyl chloride (0.15 mole) is added. After washing the organic phase with water at the ambient temperature and evaporation of the ether, 9.5 g (yield 50%) of 1,3-bis(dichloroacetyl)-2-trichloromethyl-1,3-imidazolidine is obtained which melts at 192°–193° C.

EXAMPLE 9

By operating as in the first part of Example 1, but replacing the 147.5 g of chloral by 113 g of dichloroacetaldehyde (1 mole), 141 g (yield 89%) of crude 2-dichloromethyl-1,3-oxazolidine is obtained.

By operating as in the second part of Example 6, but replacing the 41 g of 2-trichloromethyl-1,3-thiazolidine by 32 g of 2-dichloromethyl-1,3-oxazolidine (0.2 mole), prepared as indicated above, 46 g (yield 85%) of 2-dichloromethyl-3-dichloroacetyl-1,3-oxazolidine is obtained.

EXAMPLE 10

By operating as in the first part of Example 1 but replacing the 61 g of monoethanolamine by 89 g of 2-amino-2-methyl-propanol (1 mole), 180 g (yield 82%) of 2-trichloromethyl-4,4-dimethyl-1,3-oxazolidine is obtained.

20.2 g of triethylamine (0.2 mole) is added to 21.8 g of the preceding product (0.1 mole) dissolved in 300 ml of chloroform. While maintaining the temperature at about 0° C., 17.6 g of dichloroacetyl chloride (0.12 mole) dissolved in 50 ml of chloroform is then added with stirring. The stirring is maintained for a further 2 to 3 hours, while the temperature is allowed to return to the ambient conditions. The reaction mixture is then taken up with water, the organic phase is separated by decantation, washed with water, then dried over magnesium sulphate. After distillation of the chloroform in vacuo, 32 g (yield 95%) of 2-trichloromethyl-3-dichloroacetyl-4,4-dimethyl-1,3-oxazolidine is obtained in the form of a viscous paste.

EXAMPLE 11

By operating as in the first part of Example 1, but replacing the 61 g of monoethanolamine by 109 g of o-amino-phenol (1 mole), 229 g (yield 96%) of 2-trichloromethyl-1,3-benzoxazoline is obtained, which has a melting point of 102° C.

5.6 g of 2-trichloromethyl-1,3-benzoxazoline (0.023 mole), prepared as indicated above, is reacted with 24 g of dichloroacetic acid anhydride (0.1 mole) in the presence of 0.5 ml of sulphuric acid. The reaction is effected at ambient temperature in 7 hours. After hydrolysis with ice-water the precipitate obtained is filtered off, then washed with a solution of sodium carbonate and extracted with ether. The ethere extract is dried over magnesium sulphate. After evaporation of the ether, a crude product is obtained which, after recrystallization from an ether-pentane mixture, gives 5.7 g (yield 70%) of 2-trichloromethyl-3-dichloroacetyl-1,3-benzoxazoline.

EXAMPLE 12

By operating as in the second part of Example 11, but replacing the 24 g of dichloroacetic acid anhydride by 10 g of acetic anhydride (0.1 mole), 4.5 g (yield 70%) of 2-trichloromethyl-3-acetyl-1,3-benzoxazoline of melting point 74° C. is obtained.

EXAMPLE 13

1st part: 60 g (1 mole) of glacial acetic acid is slowly added with stirring, at a temperature below 20° C., to a solution of 30.5 g (0.5 mole) of monoethanolamine in 350 ml of benzene. Then 155 g (0.55 mole) of bromal is added and the solution is refluxed during two hours, the water which has formed being separated by azeotropic distillation by means of a Dean-Stark apparatus.

The temperature is allowed to drop to 20° C. and the reaction mixture is neutralized by the addition of 6 N caustic soda solution (about 180 ml), while maintaining the temperature at or below 20° C. during this operation. After decantation the organic phase is separated and washed with water (three times 400 ml). Then the organic phase is dried over sodium sulphate and filtered. The benzene is distilled under vacuum (fraction passing over at 60° C. under 100 mm Hg). 136 g of an orange viscous residual liquid is thus obtained.

This product, after recrystallization from carbon tetrachloride, gives 59 g (say a yield of 36.5%) of 2-tribromomethyl-1,3-oxazolidine, which is a white solid having a melting point of 75° C.

| Elemental analysis | % Br | % N |
| --- | --- | --- |
| calculated for $C_4H_6NOBr_3$ | 74.0 | 4.3 |
| found | 74.5 | 4.3 |

2nd part: 32.5 g (0.1 mole) of 2-tribromomethyl-1,3-oxazolidine, prepared as indicated above, is dissolved in 300 ml of chloroform. 12.2 g (0.12 mole) of triethylamine is added. Then, while maintaining the temperature below 5° C., 16.2 g (0.11 mole) of dichloroacetyl chloride is added. The mixture is stirred for 2 to 3 hours, while allowing the temperature to return to ambient conditions. The reaction mixture is taken up with 1 liter of water. After decantation, the organic phase is separated and dried over sodium sulphate. After filtration, the chloroform is distilled under vacuum. 45 g of a brown viscous residual liquid is thus obtained.

After recrystallization from carbon tetrachloride, this product gives 26 g (say a yield of 60%) of 2-tribromomethyl-3-dichloroacetyl-1,3-oxazolidine which is a solid having a melting point of 125° C.

EXAMPLE 14

38.1 g (0.2 mole) of 2-trichloromethyl-1,3-oxazolidine, prepared as indicated in the 1st part of Example 1, is dissolved in 300 ml of chloroform. 25.2 g (0.25 mole) of triethylamine is added. Then, while maintaining the temperature below 5° C., 27.5 g (0.23 mole) of n-valeryl chloride is added. The mixture is stirred for 3 hours, while allowing the mixture to return to the ambient temperature. The triethylamine hydrochloride formed is extracted with 1 liter of water. After separation the organic phase is dried over sodium sulphate.

The chloroform is distilled under vacuum. 52 g (yield 98%) of crude 2-trichloromethyl-3-valeryl-1,3-oxazolidine, in the form of a yellow viscous oil, is thus obtained. The structure of the product obtained is confirmed by the infra-red spectroscopy and the elemental analysis.

| Elemental analysis | % Cl | % N |
|---|---|---|
| calculated for $C_9H_{14}NO_2Cl_3$ | 38.8 | 5.1 |
| found | 39.1 | 4.9 |

EXAMPLE 15

1st part: 72 g (1.2 mole) of glacial acetic acid is slowly added with stirring, at a temperature below 20° C., to a solution of 36.5 g (0.6 mole) of monoethanolamine in 400 ml of benzene. Then 69 g of technical dichloroacetaldehyde (93.5%) is added and the solution is refluxed during two hours, the water which has formed being separated by azeotropic distillation by means of a Dean-Stark apparatus.

The temperature is allowed to cool to 20° C. and the reaction mixture is neutralized by the addition of 6 N caustic soda solution. After separation, the organic phase is washed three times with 500 ml of water each. Then the organic phase is dried over sodium sulphate and filtered. The benzene is stripped under vacuum (fraction passing over under 60° C. at 100 mm Hg). 51 g (say a yield of 55%) of crude 2-dichloromethyl-1,3-oxazolidine, in the form of a yellow viscous liquid, is thus obtained. The structure of the product obtained is confirmed by the infra-red analysis.

2nd part: By operating as in the second part of Example 13, but using 23.5 g (0.15 mole) of 2-dichloromethyl-1,3-oxazolidine, 18 g (0.18 mole) of triethylamine and 24.3 g (0.165 mole) of dichloroacetyl chloride in 200 ml of chloroform, after the removal of the chloroform by distillation under vacuum, 39.4 g (yield 98%) of crude 2-dichloromethyl-3-dichloroacetyl-1,3-oxazolidine is obtained.

After recrystallization from $CCl_4$, this product gives a solid having a melting point of 80° C. and of which the elemental analysis is as follows:

| | % Cl | % N |
|---|---|---|
| calculated for $C_6H_7NO_2Cl_4$ | 53.2 | 5.25 |
| found | 52.6 | 4.8 |

The structure of the product obtained is confirmed by the infra-red analysis.

This product is identical with the product obtained in Example 9.

EXAMPLE 16

By operating as in the first part of Example 15, but using 38.5 g (0.5 mole) of 2-amino-thioethanol, 60 g (1 mole) of acetic acid and 90 g chloral in 300 ml of benzene, 94.5 g of crude 2-trichloromethyl-1,3-thiazolidine, a yellow viscous liquid is obtained. After recrystallization from $CCl_4$, solid with a melting point of 75° C. is obtained. The structure of the product is confirmed by the infra-red and elemental analyses:

| | % Cl | % S | % N |
|---|---|---|---|
| calculated for $C_4H_6NSCl_3$ | 51.4 | 15.5 | 6.8 |
| found | 52.4 | 15.6 | 6.4 |

By operating as in Example 14, but using 206.5 g (1 mole) of 2-trichloromethyl-1,3-thiazolidine, 122 g (1.2 mole) of triethylamine and 162 g (1.1 mole) of dichloroacetyl chloride in 1500 ml of chloroform, 315 g of crude 2-trichloromethyl-3-dichloroacetyl-1,3-thiazolidine is obtained which, after recrystallization from a 90-10 carbon tetrachloride-chloroform mixture, gives a solid melting at 120° C. The structure of the product obtained is confirmed by infra-red and elemental analyses:

| | % Cl | % S | % N |
|---|---|---|---|
| calculated for $C_6H_6NOSCl_5$ | 56 | 10.05 | 4.4 |
| found | 55 | 9.5 | 4.5 |

This product is identical with the product obtained in Example 6.

EXAMPLE 17

A solution of 22 g (0.12 mole) of 90% p-nitroperbenzoic acid in 500 ml of methylene chloride is slowly added, while maintaining the temperature between −5° C. and −10° C., to a solution of 31.7 g (0.1 mole) of 2-trichloromethyl-3-dichloroacetyl-1,3 thiazolidine in 200 ml of methylene chloride. The addition is carried out with stirring. Then the reaction mixture is stirred for 4 further hours, the temperature being ambient. Then the reaction mixture is cooled to 0° C. and the p-nitrobenzoic acid which has formed is separated by filtration. The filtrate is washed with a dilute aqueous solution of sodium carbonate, then with water. After separation the organic phase is dried on sodium sulfate. The methylene chloride is removed by distillation under vacuum. 31.5 g (yield 94%) of 1-oxo-2-trichloromethyl-3-dichloroacetyl-1,3-thiazolidine, which is white solid melting at 140° C., is thus obtained. The structure of the product is confirmed by the infra-red and elemental analysis:

| | % Cl | % S | % N |
|---|---|---|---|
| calculated for $C_6H_6NO_2SCl_5$ | 53.2 | 9.6 | 4.2 |
| found | 52.7 | 9.3 | 4.1 |

EXAMPLE 18

By operating as in Example 17, but using 25.4 g (0.08 mole) of 2-trichloromethyl-3-dichloroacetyl-1,3-thiazolidine, 55 g (0.3 mole) of 90% p-nitroperbenzoic acid and 900 ml of methylene chloride, 25.4 g (yield 91%) of 1,1-dioxo-2-trichloromethyl-3-dichloroacetyl-1,3-thiazolidine is obtained which is a white solid melting at 105° C.

The structure of the product is confirmed by its infra-red spectrum.

This product is identical with the product obtained in Example 7.

EXAMPLE 19

A supporting soil comprising two parts by weight of clay and three parts by weight of sand (Fontainebleau ground sandstone) is placed in pans in a greenhouse. On this soil are placed, along two furrows of 0.5 cm in depth, 10 maize seeds and, between the maize seeds, 20 seeds of barley.

The sowings thus made are separated into 3 lots. On the first lot a 2 cm thick soil layer having the same composition as the supporting soil is spread, but in which by mechanical agitation a herbicide and an antidote has been incorporated according to the invention in the form of their aqueous suspensions. On the second lot a 2 cm thick soil layer of the same composition as the supporting soil, in which only the herbicide has been incorporated. Finally, on the third lot a 2 cm thick layer of the supporting soil treated with water is spread.

The amounts of herbicide applied correspond to doses of 5 and 10 kg herbicide per hectare and that of the antidote to a dose of 0.5 and 1 kg per hectare. The herbicides used belong to the family of the thiolcarbamates. These are ethyl N,N-dipropylthiolcarbamate (EPTC) and ethyl N,N-diisobutylthiolcarbamate ("Butylate"). The antidotes tested according to the invention are the compounds from Examples 1, 2, 3, 5, 6, 8, 10, 13, 14, 15, 17 and 18.

The tests corresponding to the different types of treatment have been repeated five times and the average results have been recorded for each type of treatment.

The sowings, treated on day J, are examined after 12 days (J+12) and 20 days (J+20). It has been found that, the barley, which served here as the adventitious plant of reference, has been destroyed 100%, both in the lots treated with the mixture herbicide+antidote and in those treated with the herbicide alone. In addition, the antidote efficiency of the compounds tested has been estimated by evaluating the vegetative energy of the maize plants treated with the herbicide+antidote mixture and my comparing it with the vegetative energy of the maize plants treated with the herbicide alone. The evaluation of the vegetative energy is done by measuring the size of the plants.

Table I

| Time of Examination | Dose of herbicide + dose of antidote | Antidote effectiveness on maize treated with EPTC | | | | | | | Herbicide alone | |
|---|---|---|---|---|---|---|---|---|---|---|
| | | Herbicide + antidote product | | | | | | | | |
| | | Antidote product of the examples | | | | | | | | |
| | | 1 | 6 | 5 | 8 | 10 | 3 | 2 | Dose | |
| J + 12 | 5 + 0.5 kg/ha | 108 | 118 | 119 | 109 | 109 | 157 | 138 | 5 kg/ha | 100 |
| | 0 + 0 kg/ha (control not treated) | 110 | 117 | 117 | 117 | 138 | 138 | 138 | | |
| J + 20 | 5 + 0.5 kg/ha | 109 | 135 | 135 | 115 | 115 | 173 | 159 | 5 kg/ha | 100 |
| | (Control not treated) | 115 | 134 | 134 | 134 | 150 | 150 | 150 | | |
| J + 12 | 10 + 1 kg/ha | 129 | 119 | 148 | 155 | 109 | 147 | 135 | 10 kg/ha | 100 |
| | (Control not treated) | 135 | 157 | 157 | 157 | 158 | 158 | 158 | | |
| J + 20 | 10 + 1 kg/ha | 147 | 149 | 165 | 158 | 99 | 222 | 198 | 10 kg/ha | 100 |
| | (Control not treated) | 148 | 181 | 181 | 181 | 217 | 217 | 217 | | |

| Time of Examination | Dose of Herbicide + Dose Of Antidote | Antidote effectiveness of the products on maize treated with EPTC | | | | | Herbicide Alone | |
|---|---|---|---|---|---|---|---|---|
| | | Herbicide + Antidote Product | | | | | | |
| | | Antidote Product Of The Examples | | | | | | |
| | | 13 | 14 | 18 | 17 | 15 | Dose | |
| J + 12 | 5 + 0.3 kg/ha | 128 | 95 | 86 | 105 | 125 | 5 kg/ha | 100 |
| | 0 + 0 kg/ha (control) | 133 | 133 | 133 | 133 | 133 | — | — |
| J + 20 | 5 + 0.5 kg/ha | 141 | 106 | 72 | 130 | 162 | 5 kg/ha | 100 |
| | control | 162 | 162 | 162 | 162 | 162 | — | — |
| J + 12 | 10 + 1,-kg/ha | 147 | 126 | 143 | 164 | 201 | 10 kg/ha | 100 |
| | control | 212 | 212 | 212 | 212 | 212 | — | — |
| J + 20 | 10 + 1,-Kg/ha | 208 | 127 | 146 | 240 | 321 | 10 kg/ha | 100 |
| | control | 310 | 310 | 310 | 310 | 310 | — | — |

TABLE II

| Time of Examination | Dose of hercide + Dose of antidote | Antidote effectiveness on maize from which weeds treated with butylate | | | | | | | Herbicide alone | |
|---|---|---|---|---|---|---|---|---|---|---|
| | | Herbicide + antidote product | | | | | | | | |
| | | antidote product of the examples | | | | | | | | |
| | | 1 | 6 | 5 | 8 | 10 | 3 | 2 | Dose | |
| J+12 | 5 + 0,5 kg/ha | 79 | 94 | 92 | 99 | 80 | 127 | 116 | 5 kg/ha | 100 |
| | control not treated | 112 | 105 | 91 | 91 | 112 | 112 | 112 | | |
| J+20 | 5 + 0,5 kg/ha | 109 | 102 | 110 | 110 | 71 | 138 | 124 | 5 kg/ha | 100 |
| | control not treated | 87 | 105 | 88 | 88 | 114 | 114 | 114 | | |
| J+12 | 10 + 1 kg/ha | 77 | 103 | 90 | 92 | 101 | 141 | 125 | 10 kg/ha | 100 |
| | control not treated | 162 | 105 | 102 | 102 | 138 | 138 | 138 | | |

TABLE II-continued

Antidote effectiveness on maize from which weeds treated with butylate

| Time of Examination | Dose of hercide + Dose of antidote | Herbicide + antidote product | | | | | | | Herbicide alone | |
|---|---|---|---|---|---|---|---|---|---|---|
| | | antidote product of the examples | | | | | | | Dose | |
| | | 1 | 6 | 5 | 8 | 10 | 3 | 2 | | |
| J+20 | 10 + 1 kg/ha | 156 | 121 | 125 | 114 | 113 | 172 | 160 | 10 kg/ha | 100 |
| | control not treated | 89 | 128 | 125 | 125 | 163 | 163 | 163 | | |

The average results obtained are shown in Tables I and II. In these Tables, the size of the maize plants treated with the herbicide+antidote mixture is expressed in a percentage of the size of the plants of maize treated with the herbicide alone. On these Tables it can be seen that, in the case of the maize treated with EPTC or "Butylate", the antidote effectiveness is particularly marked for the compounds of Examples 2 and 3.

EXAMPLE 20

In small plastic boat-shaped receptacles is placed a supporting soil comprising 2 parts by weight of clay and 3 parts by weight of sand. The cultivated plant to be tested as well as an adventitious plant considered as a reference weed are sown therein. The choice of the latter is linked to the choice of the herbicide which will be used. The combinations shown in the following Table have been tested.

| Herbicides | | | |
|---|---|---|---|
| Names | Doses Employed | Cultivated Plant | Adventitious Plant |
| Carbamates: | | | |
| Ethyl N,N-diethylthiol-carbamate (ETHIOLATE) | 5 kg/ha | maize | mustard |
| Ethyl N,N-cyclohexamethyl-enethiolcarbamate (MOLINATE) | 10 kg/ha | rice | mustard |
| Ethyl N-ethyl-N-cyclohexylthiolcarbamate (CYCLOATE) | 5 kg/ha | beetroot | barley |
| 2,3-dichloro-Propenyl N,N-diisopropylthiolcarbamate (DIALIATE) | 5 kg/ha | sunflower | barley |
| 4-chloro-butynyl 3-chloro-phenylcarbamate (BARBAN) | 5 kg/ha | barley | oats |
| 4-chloro-butynyl 3-chloro-phenylcarbamate (BARBAN) | 5 kg/ha | wheat | oats |
| Ethyl-N,N-diisopropyl-thiolcarbamate | 5 kg/ha | maize | barley |
| UREAS: | | | |
| 3-Chloro-4-methyl-phenyl-dimethylurea (CHLORTOLURON) | 5 kg/ha | wheat | mustard |
| 3,4-Dichloro-phenyl-methoxymethylurea (MINURON) | 10 kg/ha | maize | mustard |
| CHLOROACETANILILES: | | | |
| N-chloroacetyl-N-isopropylaniline (PROPACHLOR) | 10 kg/ha | wheat | barley |
| N-chloroacetyl-N-methoxymethyl-2,6-diethyl-aniline (ALACHLOR) | 5 kg/ha | wheat | mustard |
| TRIAZINES: | | | |
| 2-chloro-1-ethylamino-d-isopropylamino-1,3,5-triamine (ATRAZINE) | 5 kg/ha | wheat | oats |

The prepared sowings are separated into 3 lots. The first lot is covered with a layer of soil in which by mechanical agitation, a herbicide and an antidote has been incorporated, according to the invention, the second lot is covered with a layer of earth in which the herbicide only has been incorporated and the third lot is covered with a layer of non-treated soil and serves as control.

The amounts of herbicide applied correspond to doses of herbicide of 5 and 10 kg per hectare. The doses of antidote are equal to 10 percent or to half of the doses of herbicide. The antidotes tested according to the invention are the compounds of Examples 1 and 3.

The sowings are examined 12 days (J+12) and 20 days (J+20) after treatment. It has been found that, the plants chosen as reference weeds have been destroyed up to 100% both in the lots treated with the herbicide+antidote mixture, including both doses of antidote, as well as in the lots treated with herbicide alone. In addition, the antidote efficiency of the compounds tested has been estimated by the method described in the preceding Example; namely, evaluation of the vegetative energy by measuring the size of the plants in reference to the control plants. The results obtained are given in Tables III and IV. In these Tables the size of the plants treated with the herbicide+antidote mixture is expressed as a percentage of the size of the plants treated with the herbicide alone. The values between parentheses correspond to the size of the untreated control plants. It can be seen from these Tables that the products tested have an antidote action particularly interesting in the following associations: wheat/Propachlor, wheat/Alachlore, wheat/Atrazine and rice/-Molinate.

EXAMPLE 21

In this Example the antidote effect of the product of Example 1 has been tested against the herbicide EPTC applied to maize, while varying the method of application of the antidote.

The sowings of maize are separated into four lots. The first lot is covered with soil not treated and serves as control. The second lot is covered with soil in which herbicide granules have been incorporated. The third lot is covered with soil treated by incorporation with herbicide granules impregnated with the antidote; the concentration of the antidote in the granules being 10% of the concentration of herbicide. Finally, the fourth lot is covered with soil treated by incorporation of herbicide granules then immediately thereafter by an incorporation of an aqueous suspension of the antidote, the amout of antidote applied being calculated so as to be one tenth of the herbicide's dose.

The tests have been carried out at three different dosage levels of the herbicide (2.5, 5 and 10 kg/ha).

The sowings are examined 12 days and 20 days after treatment. The antidote effectiveness of the product tested is estimated as indicated previously; namely, evaluation of the vegetative energy by measuring the size of the plants. The results are given in Table V. In this Table the size of the plants treated with the herbicide+antidote mixtures is expressed in a percentage of the size of the plants treated with the herbicide alone and the numerals between parentheses correspond to the size of the untreated control plants.

It has been found that the both methods of application of the antidote ensure a good protection of the crop plant, with a slightly higher effectiveness when the herbicide and the antidote are separately incorporated.

EXAMPLE 22

In this test, the product of Example 1 has been put in the form of a powder containing 50% of product and applied as a seed dressing to the maize. The quantities of product applied per quintal of seeds were:

$D_1 = 31.25$ g
$D_2 = 62.5$ g
$D_3 = 125$ g
$D_4 = 250$ g

The sowings have been prepared as in the preceding examples and have been separated into 6 lots:

lot no. 1: not treated maize covered with not treated soil.

lot no. 2: not treated maize covered with soil in which EPTC has been incorporated.

lots no. 3, 4, 5, 6: maize treated with the doses $D_1$, $D_2$, $D_3$, $D_4$ respectively of the product of Example 1 and covered with soil in which EPTC has been incorporated.

In all the tests the dose of EPTC used was 5 kg/ha.

TABLE III

Antidote Action Of The Compounds Of Examples 1 And 3 On Various "Cultivated Plant/Herbicide" Combinations

| Antidote Product | Dose Of Antidote | Time Of Rotation | Chlor-Toluron H = 5 kg/ha wheat | Linuron H = 10 kg/ha maize | Propachlore H = 10 kg/ha wheat | Alachlore H = 5 kg/ha wheat | Atrazine H = 5 kg/ha wheat |
|---|---|---|---|---|---|---|---|
| Product of Example 1 | H × 1/10/ha | J + 12 | 107 (130) | 100 (147) | — | 150 (110) | 195 (193) |
|  |  | J + 20 | — | 105 (200) | 186 (250) | 180 (192) | — |
|  | H × ½/ha | J + 12 | 99 (130) | 100-(147) | — | 140 (110) | 195 (193) |
|  |  | J + 20 | — | 100 (200) | 184 (250) | 180 (192) | — |
| Product of Example 3 | H × 1/10/ha | J + 12 | 105 (130) | 100 (147) | — | 115 (110) | 190 (193) |
|  |  | J + 20 | — | 115 (200) | 155 (250) | 120 (192) | — |
|  | H × ½/ha | J + 12 | 106 (130) | 105 (147) | — | 120 (110) | 195 (193) |
|  |  | J + 20 | — | 108 (200) | 131 (250) | 125 (192) | — |

TABLE IV

Antidote Action Of The Compounds Of Examples 1 and 3 On Various "Cultivated Plant/Herbicide" Combinations

| Antidote Product | Dose Of Antidote | Time Of Notation | Ethiolate H=5 kg/ha maize | Molinate H=10 kg/ha rice | Cycloate H=10 kg/ha beetroot | Diallate H=5 kg/ha sunflower | Barbane H=5 kg/ha barley | Barbane H=5 kg/ha wheat | N-N diisopropylthiocarbamete 5 kg/ha maize |
|---|---|---|---|---|---|---|---|---|---|
| Ex. 1 | H × 1/10/ha | J+12 | 110 (111) | 100 (105) | 96 (113) | 100 (87) | 108 (137) | 125 (169) | 105 (112) |
|  |  | J+20 | 116 (122) | 110 (120) | 109 (112) | 94 (67) | 116 (128) | 108 (100) | 112 (120) |
|  | H × ½/ha | J+12 | 110 (111) | 110 (105) | 85 (113) | 90 (87) | 103 (137) | 102 (169) | 108 (112) |
|  |  | J+20 | 120 (122) | 120 (120) | 108 (112) | 89 (67) | 117 (128) | 94 (100) | 115 (128) |
| Ex. 3 | H × 1/10/ha | J+12 | 131 (111) | 105 (105) | 98 (113) | 96 (87) | 99 (137) | 77 (169) | 125 (122) |
|  |  | J+20 | 150 (122) | 115 (120) | 116 (122) | 107 (67) | 107 (128) | 100 (100) | 140 (120) |
|  | H × ½/ha | J+12 | 135 (111) | 110 (105) | 102 (113) | 93 (87) | 101 (137) | 87 (169) | 130 (112) |
|  |  | J+20 | 149 (122) | 125 (120) | 94 (112) | 96 (67) | 107 (128) | 96 (100) | 145 (120) |

TABLE V

INFLUENCE OF THE METHODS OF APPLICATION ON THE ANTIDOTE ACTION OF THE PRODUCT OF EXAMPLE 1 IN CONNECTION WITH EPTC

| METHODS OF APPLICATION | TIME OF NOTATION | E.P.T.C. + antidote Dose of herbicide + dose of antidote | | |
|---|---|---|---|---|
|  |  | 2.5 + 0.25 kg/ha | 5 + 0.5 kg/ha | 10 + 1 kg/ha |
| Incorporation of antidote in the granulated herbicide | J + 12 | 86 (99) | 105 (110) | 114 (135) |
|  | J + 20 | 85 (99) | 112 (115) | 130 (148) |
| Separate applications (1) Granulated herbicide | J + 12 | 97 (99) | 109 (110) | 130 (135) |
| (2) Antidote | J + 20 | 97 (99) | 110 (115) | 147 (148) |

The vegetative energy of the maize plants has been evaluated after 12 days and 20 days. The results obtained are shown in Table VI. In this table the vegetative energy of the plants is expressed in a percentage of the vegetative energy of the plants treated with the herbicide alone.

TABLE VI

ANTIDOTE ACTION BY TREATMENT OF THE SEEDS

| TREATMENT | TIME OF EXAMINATION | VEGETATIVE ENERGY |
|---|---|---|
| EPTC + 1 (D$_1$) | J + 12 | 159 |
|  | J + 20 | 287 |
| EPTC + 1 (D$_2$) | J + 12 | 189 |
|  | J + 20 | 363 |
| EPTC + 1 (D$_3$) | J + 12 | 185 |
|  | J + 20 | 348 |
| EPTC + 1 (D$_4$) | J + 12 | 188 |
|  | J + 20 | 369 |
| EPTC alone | J + 12 | 100 |
|  | J + 20 | 100 |
| NOT TREATED CONTROL | J + 12 | 192 |
|  | J + 20 | 358 |

We claim:

1. The compound 2-trichloromethyl-3-dichloroacetyl-1,3-tetrahydrooxazine.

2. The compound 2-trichloromethyl-3-dichloroacetyl-1,3-oxazolidine.

3. The compound 2-trichloromethyl-3-dichloroacetyl-5-methyl-1,3-oxazolidine.

4. The compound 2-trichloromethyl-3-dichloroacetyl-4-ethyl-1,3-oxazolidine.

5. The compound 2-dichloromethyl-3-dichloroacetyl-1,3-oxazolidine.

6. The compound 2-tribromomethyl-3-dichloroacetyl-1,3-oxazolidine.

7. A composition for increasing the selectivity of the herbicides belonging to the thiolcarbamates, the chloroacetanilides, the ureas, the triazines, the carbamates and the uracils families or mixtures thereof, which comprises an antidotally effective amount of a compound selected from the group consisting of:
2-trichloromethyl-3-dichloroacetyl-1,3-oxazolidine;
2-trichloromethyl-3-dichloroacetyl-5-methyl-1,3-oxazolidine;
2-trichloromethyl-3-dichloroacetyl-4-ethyl-1,3-oxazolidine;
2-trichloromethyl-3-dichloroacetyl-1,3-tetrahydrooxazine;
2-dichloromethyl-3-dichloroacetyl-1,3-oxazolidine; and
2-tribromomethyl-3-dichloroacetyl-1,3-oxazolidine,
and additives commonly used with a view to facilitate the keeping, operation and penetration of the products in the plants.

8. A composition for selectively controlling the growth of unwanted plants among cultivated plants, which comprises a herbicidally effective amount of a herbicide belonging to the thiolcarbamates, the chloroacetanilides, the ureas, the triazines, the carbamates and the uracils families, an antidotally effective amount of a compound selected from the group consisting of:
2-trichloromethyl-3-dichloroacetyl-1,3-oxazolidine;
2-trichloromethyl-3-dichloroacetyl-5-methyl-1,3-oxazolidine;
2-trichloromethyl-3-dichloroacetyl-4-ethyl-1,3-oxazolidine;
2-trichloromethyl-3-dichloroacetyl-1,3-tetrahydrooxazine;
2-dichloromethyl-3-dichloroacetyl-1,3-oxazolidine; and
2-tribromomethyl-3-dichloroacetyl-1,3-oxazolidine,
and additives commonly used with a view to facilitate the keeping, operation and penetration of the products in the plants.

9. A composition as defined in claim 8, wherein the herbicide is ethyl N,N-dipropylthiolcarbamate.

10. A method for treating soil to protect the cultivated plant therein from injury by herbicides which comprises applying to the soil, before or after the emergence of the plant and before or after application of the herbicide, an antidotally effective amount of a compound selected from the group consisting of:
2-trichloromethyl-3-dichloroacetyl-1,3-oxazolidine;
2-trichloromethyl-3-dichloroacetyl-5-methyl-1,3-oxazolidine;
2-trichloromethyl-3-dichloroacetyl-4-ethyl-1,3-oxazolidine;
2-trichloromethyl-3-dichloroacetyl-1,3-tetrahydrooxazine;
2-dichloromethyl-3-dichloroacetyl-1,3-oxazolidine; and 2-tribromomethyl-3-dichloroacetyl-1,3-oxazolidine.

11. A method for treating seeds of a cultivated plant to protect the plant born of said seeds from injury by herbicides which comprises applying thereto an antidotally effective amount of a compound selected from the group consisting of:
2-trichloromethyl-3-dichloroacetyl-1,3-oxazolidine;
2-trichloromethyl-3-dichloroacetyl-5-methyl-1,3-oxazolidine;
2-trichloromethyl-3-dichloroacetyl-4-ethyl-1,3-oxazolidine;
2-trichloromethyl-3-dichloroacetyl-1,3-tetrahydrooxazine;
2-dichloromethyl-3-dichloroacetyl-1,3-oxazolidine; and
2-tribromomethyl-3-dichloroacetyl-1,3-oxazolidine.

12. A method for selectively controlling the growth of unwanted plants among cultivated plants, which comprises applying to the soil, before or after the emergence, a composition as defined in claim 8.

* * * * *